United States Patent
Bolz et al.

[11] Patent Number: 5,970,986
[45] Date of Patent: Oct. 26, 1999

[54] APPARATUS FOR REJECTION DIAGNOSTICS AFTER ORGAN TRANSPLANTS

[75] Inventors: Armin Bolz; Max Schaldach, both of Erlangen, Germany

[73] Assignee: Biotronik Mess- und Therapiegeräte GmbH & Co. Ingenieurbüro Berlin, Berlin, Germany

[21] Appl. No.: 08/929,787

[22] Filed: Sep. 15, 1997

[30] Foreign Application Priority Data

Sep. 20, 1996 [DE] Germany .......................... 196 38 585

[51] Int. Cl.⁶ ..................................................... A61N 5/00
[52] U.S. Cl. ............................ 128/899; 600/500; 600/508
[58] Field of Search ............................ 128/903, 897–898; 600/345, 300, 547, 508, 519, 518, 500–503, 521, 510

[56] References Cited

U.S. PATENT DOCUMENTS

| | | | |
|---|---|---|---|
| 3,971,362 | 7/1976 | Pope et al. | 128/2 P |
| 4,655,170 | 4/1987 | DaSilva | 128/903 |
| 4,681,111 | 7/1987 | Silvian | 128/903 |
| 5,139,028 | 8/1992 | Steinhaus et al. | |
| 5,252,962 | 10/1993 | Urbas et al. | 128/903 |
| 5,331,966 | 7/1994 | Bennet et al. | 128/696 |
| 5,411,031 | 5/1995 | Yomtov . | |
| 5,415,181 | 5/1995 | Hogrefe et al. | |
| 5,697,384 | 12/1997 | Miyawaki et al. | 128/903 |
| 5,704,352 | 1/1998 | Tremblay et al. | 600/300 |
| 5,716,407 | 2/1998 | Knapp et al. | 128/903 |
| 5,790,107 | 8/1998 | Kasser et al. | 345/174 |

FOREIGN PATENT DOCUMENTS

| | | |
|---|---|---|
| 0 476 242 | 3/1992 | European Pat. Off. . |
| 2193320 | 2/1974 | France . |
| 32 19 558 | 12/1983 | Germany . |
| 41 25 746 | 2/1992 | Germany . |
| 41 00 568 | 7/1992 | Germany . |
| 43 17 340 | 12/1994 | Germany . |
| 43 41 903 | 6/1995 | Germany . |
| 295 08 772 | 9/1995 | Germany . |
| 195 38 213 | 4/1996 | Germany . |
| 9401174 | 1/1994 | WIPO . |
| WO 94/04094 | 3/1994 | WIPO . |

OTHER PUBLICATIONS

T. Akin et al., "A telemetrically powered and controlled implantable neural recording system with CMOS interface circuitry", Proceedings of the Mediterranean Electrotechnical Conference, pp. 545–548, Apr. 4, 1994.

Foster, I.C., "Preliminary development of a radiotelemetry system for biological applications.", Medical & Biological Engineering & Computing, s. 281–291 (May 1986).

Ko, Wen et al., "Single frequency RF powered ECG telemetry system.", IEEE Transactions On Biomedical Engineering, vol. BME–26, No. 2, pp. 105–109 (Feb. 1979).

*Primary Examiner*—Robert L. Nasser
*Assistant Examiner*—Michael Astorino
*Attorney, Agent, or Firm*—Browdy and Neimark

[57] ABSTRACT

An apparatus for rejection diagnostics after organ transplantations is provided with
- an extracorporal base station with a high frequency transmitter and receiver unit, and
- a telemetric rejection sensor implantable in a patient's body, comprising
  - a high frequency receiver unit for receiving high frequency signals from the base station,
  - a rectifier and decoder unit for converting the high frequency signals received into a supply voltage and control records for the rejection sensor,
  - an energy storage for storing the supply voltage,
  - a control unit for controlling the measuring processes within the apparatus,
  - a sensor arrangement controlled by the control unit and to be brought into contact with the organ to be monitored and having measuring electrodes for measuring rejection-specific variables,
  - an encoder unit for converting the measured variables into corresponding data signals, as well as
  - a high frequency emitter unit for transmitting the data signals produced by the encoder unit to the extracorporal base station.

15 Claims, 2 Drawing Sheets ness of the transplanted organ and any possible rejection reaction.
APPARATUS FOR REJECTION DIAGNOSTICS AFTER ORGAN TRANSPLANTS

BACKGROUND OF THE INVENTION

1. Field of the Invention

The invention relates to an apparatus for rejection diagnostics after organ transplantations.

2. Background Art

As regards the background of the present invention, a main post transplantation problem resides in a possible rejection of the transplanted organ due to a corresponding defense reaction of a patient's body. For this to be prevented, medicinal immunosuppression is carried out, which is meant to suppress the rejection reactions.

This medicinal immunosuppression has considerable side effects so that patient after-care is always accompanied with the conflict of too high an immunosuppression—and the possibly lethal consequences of an infection—and too low an immunosuppression—having the possibly lethal consequences of an acute rejection reaction. For these reasons, the tendency is to manage with minimum base therapy and to diagnose possible rejection episodes at an early stage, which can then still be parried by an immediately increased dose of drugs. For this type of therapy to be put into practice, a method must be available which permits the rapid diagnosis of a rejection reaction. To date, biopsy is customary in this regard, tissue being taken micro-invasively from the transplanted organ and then being examined hisologically. It is possible to infer from the result of these histological examinations that rejection reactions are to be expected.

A drawback of such a biopsy control resides in the fact that it is rather complicated and costly. Biopsies have to take place at a rhythm ranging between two weeks and two months, this meaning that each time, a micro-invasive operation is necessary, which is troublesome to the patient.

Approaches to solve these problems consist in that electric signals of reaction to stimulus of the transplanted organ are analyzed, from which conclusions are made, regarding the latter's condition and any possible rejection reaction. However, this is not an established method of diagnosis so far and it can only be used in the case of transplanted hearts, only hearts manifesting corresponding signals of reaction to stimulus. Consequently, other transplantation organs cannot be monitored. Moreover, another drawback resides in that a complete heart-pacemaker systems comprising ECG telemetry must be implanted for this method of diagnosis to be possible. Such heart-pacemaker systems have some size owing to the integrated battery and they have only a limited lifetime. Once the battery is exhausted, the heart-pacemaker system must be replaced, which does not predestine it to long-term use in diagnostic rejection investigation.

SUMMARY OF THE INVENTION

Proceeding from the prior art problems specified, it is the object of the invention to make available an apparatus for the rejection diagnostics after organ transplantations, which, on the one hand, is implantable for information on the condition of the transplanted organ to be obtained telemetrically at any time, but which, on the other hand, is not governed by the restrictions of the complete heart-pacemaker systems mentioned above.

Accordingly, provision is made for an apparatus for rejection diagnostics after organ transplantations which is equipped with an extracorporal base station comprising a high frequency transmitter and receiver unit. Furthermore, provision is made for a telemetric rejection sensor to be implanted in a patient's body, which comprises

- a high frequency receiver unit for receiving high frequency signals from the base station,
- a rectifier and decoder unit for converting the high frequency signals received into a supply voltage and control records for the rejection sensor,
- an energy storage for storing the supply voltage,
- a control unit for controlling the measuring processes within the apparatus,
- a sensor arrangement controlled by the control unit and to be brought into contact with the organ to be monitored and having measuring electrodes for measuring rejection-specific variables,
- a encoder unit for converting the variables furnished by the sensor arrangement into corresponding data signals, and
- a high frequency emitter unit for transmitting the data signals generated by the encoder unit to the extracorporal base station.

As becomes apparent from the preceding list of features, the apparatus according to the invention no longer has a battery as it is necessary in active prior art implants. In this regard, the apparatus is not subject to any restricion of lifetime by energy supply. Rather, the apparatus according to the invention is a passive system, i.e. working without a battery, in which the input of the necessary energy for the power supply of the individual components takes place from outside. Such an input is fundamentally known from the prior art in the most varying fields as a so-called "transponder system". For instance transponder systems are used for the identification of objects or for theft protection in vehicles. From WO94/04094 it is for instance known to provide prostheses such as breast implants with an encoded transponder which can be interrogated externally by a reader so that for example transplantation data and manufacturers details can be read out.

Fundamentally, in such transponder systems, a high frequency carrier frequency in the range of some 100 kHz upwards is put in externally and—depending on the system design—as a rule used for charging a supply capacitor which, in turn, supplies energy to a transmitter for retransmission of the data stored in the transponder.

The invention proceeds from the idea that by integrating a measuring device for electric variables specific of rejection into an implantable transponder system, reliable and durable monitoring of the respective transplant for any imminent rejection reactions is possible. The rejection sensor can be designed such that various measuring tasks are combined, such as the measurement of autonomous electric variables (for instance intracardiac ECG), the measurement of electric responses to stimulus (so-called "evoked electric variables"), the measurement of tissue impedance and the measurement of the stimulus conduction velocity in the monitored transplant. If several of these measuring methods are combined, then the rejection sensor must be designed as a multiplex system to be programmed from outside. However, the rejection sensor can be configured for a desired measuring task right from the start.

In keeping with preferred embodiments of the diagnostics apparatus, the entire rejection sensor can be encapsulated in a molded housing of silicone material, in which the electrodes surface. The electronic components of the sensor inclusive of the measuring electrodes can be intregated on an IC component. By alternative, the virtual electronic part of the rejection sensor can be implanted as an encapsulated component under a patient's skin, the measuring electrodes being embodied as a special unit to be applied to the transplant to be monitored. This helps minimize the telemetry losses during data transmission between the extracorporal basic device and the rejection sensor. Nevertheless, any transplant in the body can be monitored by means of the measuring-electrode unit coupled with the rejection sensor via feed lines.

By advantage, the extracorporal base station can be divided into a simple receiver and transmitter and an intelligent data collection system. An example is the so-called telephone monitoring, a simple receiver and transmitter as an extracorporal base station being in the possession of the patient and controlling the measuring of the rejection sensor. The data received by the latter are passed on to a central data collection and evaluation system—for instance to a central evaluation computer stationed in a clinic.

Further features, details and advantages of the apparatus according to the invention will become apparent from the ensuing description of an exemplary embodiment and from the sub-claims, taken in conjunction with the drawings.

DESCRIPTION OF THE PREFERRED EMBODIMENT

Figures 1, 1A:
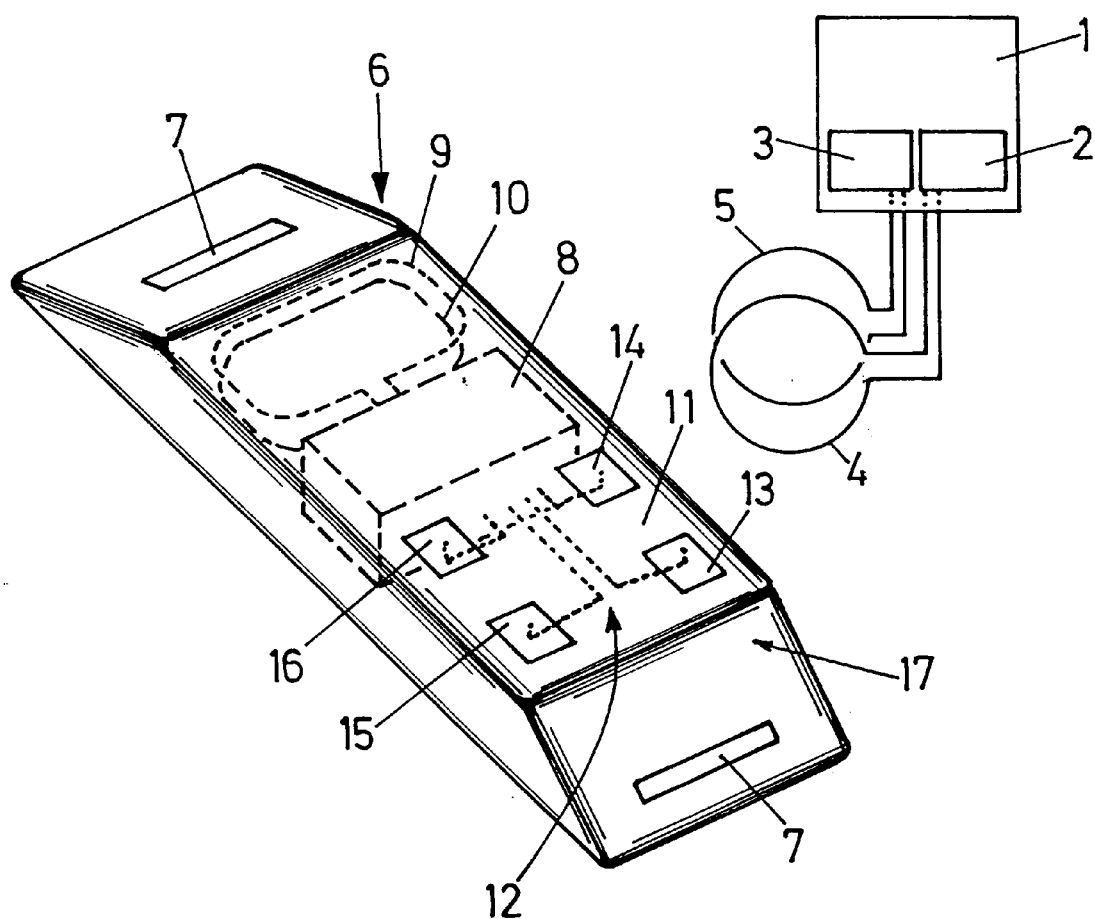
FIGS. 1 and 1A are diagrammatic illustration of a rejection sensor (FIG. 1) with an associated base station (FIG. 1)

FIGS. 1 and 1A, which are highly diagrammatic, illustrate the two main components of the apparatus according to the invention for rejection diagnostics. On the one hand, this is an extracorporal base station 1 comprising a high frequency transmitter unit 2 and a high frequency receiver unit 3. A transmitting antenna 4 and a receiving antenna 5, respectively, are allocated to the high frequency transmitter and receiver unit 2, 3, respectively, amplitude modulated (or frequency modulated) high frequency signals being transmittable between the base station 1 and the implantable rejection sensor 6 by way of these antennas, which can also be so-called antenna arrays.

During organ transplantation, the rejection sensor 6, seen highly diagrammatically and on a strongly enlarged scale in FIG. 1, is fixed on the donor organ by customary surgical fixing elements 7 (for instance surgical suture material) in such a way that electric and electronic measurements can be made on the surface of the organ in a manner still to be explained, these measurements giving information about a possibly impending rejection reaction of the transplant. Also optical measurements, thermal conductivity measurements or temperature measurements in general can be performed by the rejection sensor—depending on the application.

As outlined in FIG. 1, the electronic components of the implantable telemetric rejection sensor 6 are collected on an IC component 8, to which a receiving coil 9 and a transmitting coil 10 are allocated, by way of which the mentioned high frequency signals emitted by the base station are received or transmitted to the latter. Further, a sensor arrangement 12 comprising four miniaturized measuring electrodes 13, 14, 15, 16 is provided on one of 10 the plane surfaces 11 of the rejection sensor; these measuring electrodes 13, 14, 15, 16 appear on the surface 11. The measuring electrodes 13, 14, 15, 16 and the coils 9, 10 can also be integrated in the IC component 8.

The sensor arrangement 12, the receiving and transmitting coils 9, 10 and the IC component 8, which is a chip, are encapsulated in a molded housing 17 of silicone material. Incorporation in a titanium housing is conceivable as well.

By alternative, the sensor and the electrode arrangement can be separated—which is not shown in detail—so that the rejection sensor need not be anchored on the transplant. It is sufficient to fix the electrode arrangement, which may be a so-called "micro-electrode relay", on the transplanted organ, as known from heart pacemaker technology.

Figure 2:
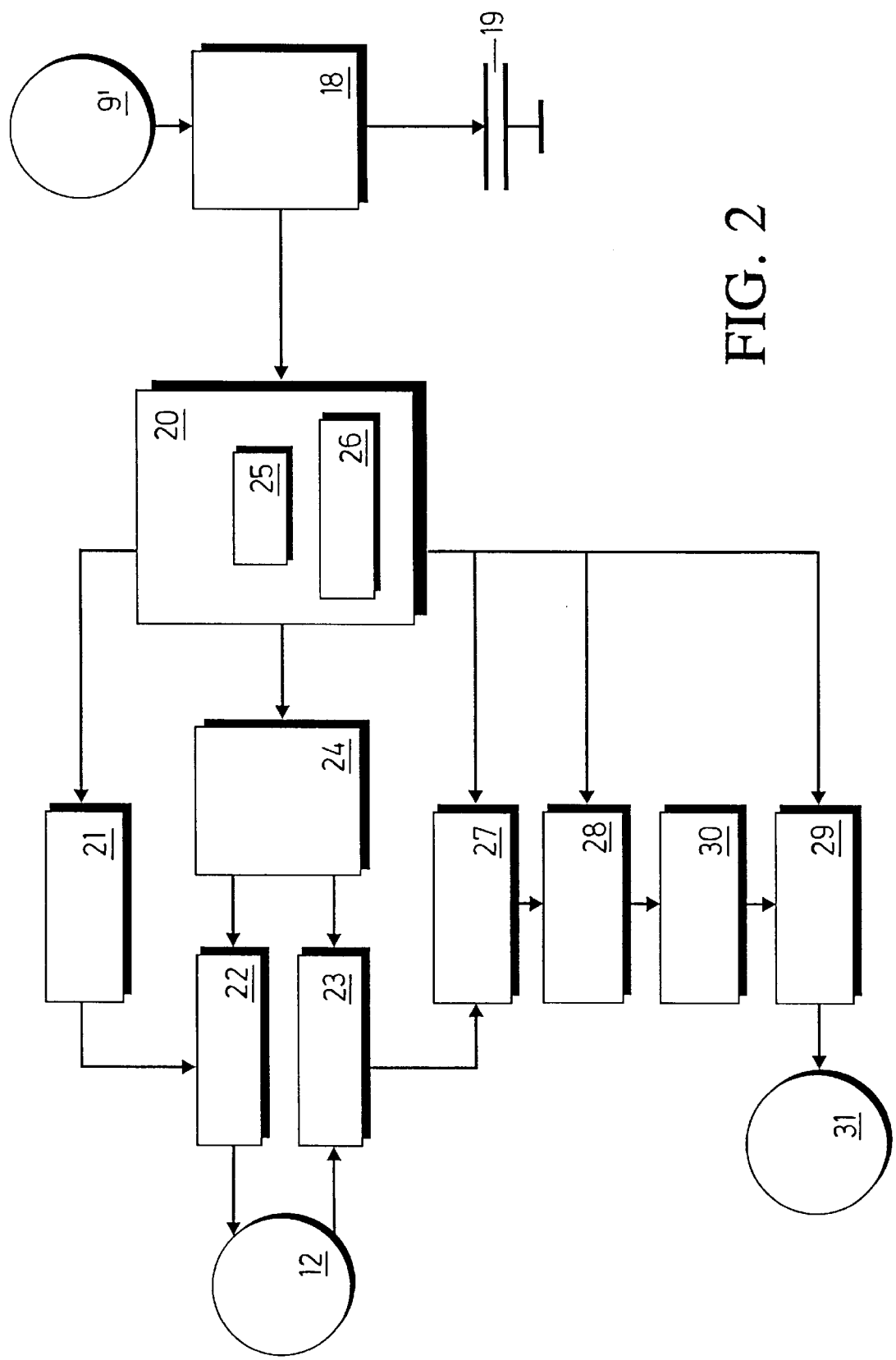
FIG. 2 is a block diagram of the components of the rejection sensor.

The structure of the virtual rejection sensor 6 is to be explained, based on FIG. 2. The receiver unit 9' comprising the receiving coil 9 is followed by a rectifier and decoder unit 18, which filters the control data for the rejection sensor 6 from the amplitude-modulated high frequency signal received and which supplies the voltage induced by the high frequency signal to a supply capacitor 19. The latter serves for the supply of voltage to all the electronic components of the rejection sensor 6, which is not illustrated in FIG. 2 for reasons of clearness. Furthermore, the supply capacitor 19 is provided with a voltage stabilizer (not shown).

The rectifier and decoder unit 18 is put into practice by a demodulation-effect network (not shown), which extracts the control data from the HF signal. The transmitted control signals serve for the selection of the measuring method and for the transmittal of the measuring parameters to be used therein. In this regard, the control signals are supplied to a control unit 20, which is disposed downstream of the rectifier and decoder unit and which controls a signal generating unit 21 and flexibly wired D/A multiplexers or A/D multiplexers 22, 23 by means of a corresponding multiplexer control logic 24. The control unit 20 further comprises a suitable timer 25 for measuring methods relevant to time to be performed, such as the measurement of the stimulus conduction velocity in the organ tissue. Moreover, a trigger unit 26 is provided in the control unit 20, triggering a signal conditioning unit 27 disposed downstream of the A/D multiplexer 23, an A/D converter 28 and a data conditioning unit 29. The signal conditioning unit 27 with the A/D converter 28 is an evaluation unit for the measuring signals. A memory 30, for instance in the form of a FIFO memory, is inserted between the A/D converter 28 and the data conditioning unit 29. The data conditioning unit 29, which proceeds with encoding the evaluated data into corresponding data signals, is topped by an HF emitter unit 31, which causes data signal transmission onto the transmitting coil 10 towards the base station 1.

If the rejection sensor 6 is to monitor the transplant in his charge for instance by measurement of the stimulus conduction velocity in the organ tissue, then a correspondingly encoded HF signal is telemetrically transmitted from the base station 1 via the HF transmitter 2 to the rejection sensor 6. The rectifier and decoder unit 18 extract the control data from this signal. Simultaneously the supply capacitor 19 is (further) charged.

The control unit 20 takes the data extracted from the HF signal and decodes them for the selection of the desired measuring method, i.e. the measuring of the stimulus conduction velocity in the present case. Based on this, the multiplex control logic 24 is triggered correspondingly by way of the signal generating unit 21. The latter adjusts the signals to be emitted to the measuring electrodes 13 to 16 of the sensor arrangement 12 for the corresponding measuring method to the measuring task. In the signal generating unit 20, alternating voltage can be produced for instance for measuring the tissue impedance or a generator for constant voltage surges can be implemented for electric responses to stimulus to be measured. The multiplexer control logic 24 controls the individual multiplexers 22, 23 producing the connection to the measuring electrodes 13 to 16 for the input and output of measuring signals.

The signals supplied by the measuring electrodes 13 to 16 of the sensor arrangement 12 to the A/D multiplexer 23 are evaluated by the signal conditioning unit 27, i.e. they are subjected for instance to filtering or averaging. The subsequent A/D converter 28 digitalizes the measuring signals for them to be intermediately stored in the memory 30. The data conditioning unit 29 encodes and concentrates the measured data for the protection against transmission errors and passes the data thus processed to the HF emitter unit 31 for corresponding data signals to be transmitted via the transmitting coil 10 to the base station 1. There, the measured data are received, converted and correspondingly displayed.

By the separation of the HF receiver unit 9'0 and the HF emitter unit 31, energy supply and control on the one hand and the data transmission on the other can take place simultaneously on two channels at varying frequencies and varying transmission rates.

As a result of the explained structure, the rejection sensor can perform various measuring methods while controlled externally. For instance, autonomous electric variables such as an ECG can be measured. Also chemical sensors are conceivable for the detection of certain chemical compositions or constituents on the transplant. During the measurement of reactions to electric stimulus, a voltage impulse is applied to the tissue via two measuring electrodes 13, 14 and a corresponding reaction of the organ to stimulus is sensed via the two other measuring electrodes 15, 16.

During the measurement of tissue impedance, alternating current of variable frequency is impressed via two measuring electrodes 13, 15 and the electrode voltage drop is measured. A complete impedance spectrum of the monitored transplant is thus established.

For the measurement of the stimulus conduction velocity, a voltage impulse is applied via two measuring electrodes 13, 14 and the time is measured until this stimulus arrives at the second pair of electrodes 15, 16. The stimulus conduction velocity can be inferred therefrom.

In a slightly simplified embodiment of the subject matter of the invention, which is not expressly illustrated, the transmitting and receiving coils 31, 9' can be united to form a single coil and the two D/A and A/D multiplexers can be combined to form a simple multiplexer. When a single antenna is used, transmitting and receiving can nevertheless take place at varying frequencies due to the use of two band-pass filters. Also, it is possible to do without the memory 30 when the measured data are transferred "on-line" to the base station by means of telemetry at a sufficiently high data rate.

The multiplexer programming of the specified rejection sensor is of advantage in order to be able to poll the various measuring methods from outside. Thus, the rejection sensor is universally usable and adjustable to changing conditions.

In the case of a corresponding medicinal indication, the rejection sensor can also be configured only for a certain application, which of course reduces the technical requirements.

What is claimed is:

1. A transponder device for rejection diagnostics of a transplant, after organ transplantations, said transponder device comprising
    an extracorporal base station (1) with a high frequency transmitter (2) which emits high frequency signals and a receiver unit (3), and
    a telemetric rejection sensor (6) implantable in a patient's body, comprising
        a high frequency receiver unit (9') for receiving the high frequency signals from the extracorporeal base station,
        a rectifier and decoder unit (18) for converting the high frequency signals received into a supply voltage and control records for the rejection sensor (6),
        an energy storage (19) for storing the supply voltage,
        a control unit (20) for controlling measuring processes within the rejection sensor,
        a sensor arrangement (12) controlled by the control unit (20) and adapted to be in contact with a transplant to be monitored and having a measuring electrode configuration for measuring rejection-specific measured variables,
        an encoder unit (29) for converting the measured variables furnished by the sensor arrangement (12) into corresponding data signals, as well as
        a high frequency emitter unit (31) for transmitting the data signals produced by the encoder unit (29) to the extracorporal base station (1).

2. The transponder device according to claim 1, wherein the energy storage (19) is a supply capacitor conductively engaged to the rectifier and the decoder unit (18).

3. The transponder device according to claim 1, wherein the high frequency receiver unit (9') is designed for receipt of amplitude or frequency modulated high frequency signals from the extracorporeal base station.

4. The transponder device according to claim 1, wherein the sensor arrangement (12) is a multiplex system.

5. The transponder device according to claim 4, wherein a D/A (22) and A/D multiplexer (23) and a multiplexer control logic are inserted between the sensor arrangement (12) and the control unit (20).

6. The transponder device according to claim 1, wherein the measuring electrode configuration comprises four measuring electrodes (13, 14, 15, 16) and which, by control through the control unit (20), are each variably interconnectable for varying measuring purposes.

7. The transponder device according to claim 1, wherein, by means of the sensor arrangement (12), transplant specific electrochemical variables, tissue impedance of the transplant, electric responses of the transplant to stimulus and/or a stimulus conduction velocity of the transplant are measurable as variables relevant to rejection.

8. The transponder device according to claim 1, wherein the components of the telemetric rejection sensor (6) are encapsulated in a molded housing (17) of silicone material, in which the measuring electrode configuration (13, 14, 15, 16) appear on a surface (11) of the molded housing (17).

9. The transponder device according to claim 1, wherein the components of the telemetric rejection sensor (6) inclusive of the measuring electrodes (13, 14, 15, 16) are integrated on an IC component.

10. The transponder device according to claim 1, wherein the telemetric rejection sensor (6) is embodied as an encapsulated component to be adapted to be implanted under a patient's skin.

11. The transponder device according to claim 1, wherein the four measuring electrodes are embodied as a separate unit to be applied to the transplant to be monitored.

12. The transponder device according to claim 1, wherein the high frequency receiver (9') and emitter unit (31) are separate and work at varying frequencies.

13. The transponder device according to claim 1, wherein the telemetric rejection sensor (6) comprises fixing elements (7) for being fixed on a surface (11) of the transplant to be monitored.

14. The transponder device according to claim 1, wherein the extracorporal base station is divided into a data receiving and transmitting device allocated to a patient.

15. The transponder device according to claim 1, wherein the extracorporal base station is divided into a central data collection and evaluation system.

* * * * *